United States Patent [19]

Halfon et al.

[11] Patent Number: 5,438,149
[45] Date of Patent: Aug. 1, 1995

[54] DIFLUOROMETHYLATION OF A PHENYL TRIAZOLINONE

[75] Inventors: Marc Halfon, Cranbury; Eric W. Sortore, Trenton, both of N.J.

[73] Assignee: FMC Corporation, Philadelphia, Pa.

[21] Appl. No.: 250,210

[22] Filed: May 27, 1994

[51] Int. Cl.$^6$ .......................................... C07D 249/12
[52] U.S. Cl. ................................................ 548/263.2
[58] Field of Search ...................................... 548/263.2

[56] References Cited

U.S. PATENT DOCUMENTS 5,125,958  6/1992  Halfon et al. ............................ 71/92

Primary Examiner—Patricia L. Morris
Attorney, Agent, or Firm—H. Robinson Ertelt; Robert M. Kennedy

[57] ABSTRACT

An improved process for the difluoromethylation of a 1-phenyl-1H-1,2,4-triazol-5-one at the 4-position of the triazole ring with chlorodifluoromethane significantly reduces the amount of base required for the process, thereby reducing the environmental impact of the process by reducing the amount of by-product salts in the waste stream. The improvement comprises reacting the triazolinone with potassium carbonate in a solvent such as dimethylformamide, at a carbonate to triazolinone ratio in the range of about 0.55 to 1.0; reducing the water content of the reaction mixture to below about 2400 ppm by distillation; heating the reaction mixture in a sealed autoclave to 110° to 180° C., adding a 10 to 15 percent molar excess of chlorodifluoromethane, heating the reaction mixture at a temperature of 140° to 210° C. for 5 to 60 minutes, and recovering the difluoromethylated triazolinone.

5 Claims, No Drawings

DIFLUOROMETHYLATION OF A PHENYL TRIAZOLINONE

This application pertains to a two step process for difluoromethylating 4,5-dihydro-3-methyl-1-phenyl-1H-1,2,4-triazol-5-one at the 4-position with chlorodifluoromethane. In the first step a solution of 4,5-dihydro-3-methyl-1-phenyl-1H-1,2,4-triazol-5-one in N,N-dimethylformamide is reacted with potassium carbonate to form the potassium salt of the triazolinone. The second step is carried out under autogenous pressure in an autoclave and involves the reaction of the salt of the triazolinone, in the presence of some potassium carbonate, with chlorodifluoromethane (Freon ® 22) in N,N-dimethylformamide to yield the 4-difluoromethyl derivative of the triazolinone. The potassium salts produced in the reaction and any excess carbonate are then filtered from the reaction mixture, leaving a solution of product in N,N-dimethylformamide, from which it can be recovered, or the solution may be used in a subsequent reaction.

The closest prior art is U.S. Pat. No. 5,125,958, in which there is described in Example 8, Step E, the difluoromethylation of 1-[4-chloro-2-fluoro-5-(1,3-dithian-2-yl)phenyl]-4,5-dihydro-3-methyl-1,2,4-triazol-5(1H)-one by means of a similar two-step process. However, this is a prospective example, which gives only amounts of reactants, but no yields. The ratio of potassium carbonate to triazolinone in this example is 3.06 on a molar basis, and both steps are carried out at atmospheric pressure. There is no suggestion in the patent that excellent yields may be obtained with substantially less potassium carbonate.

The improved process of the present invention is summarized in the following schema:

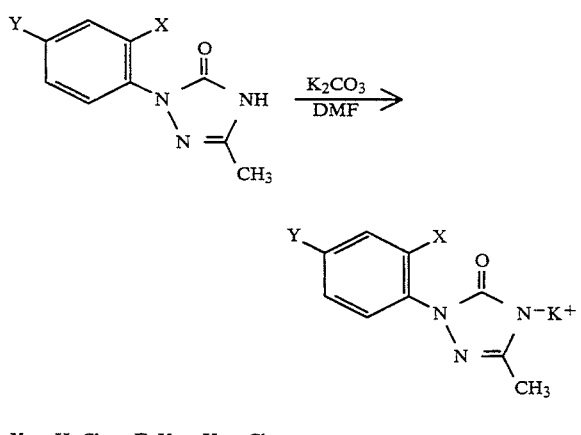

X = H, Cl, or F; Y = H or Cl

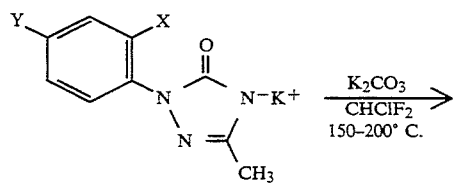

-continued

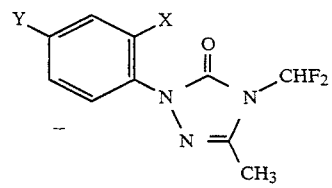

While this reaction is similar to that described generally in the patent referenced above, the patent does not suggest the reaction conditions of the present invention, such as carrying out the reaction in a sealed vessel under autogenous pressure. However, the greatest difference between the example in referenced patent and the present process is the mole ratio of potassium carbonate to the triazolinone. This ratio is reduced from 3.0 to 0.8 or even less with no loss of yield. The benefit of this reduction is to reduce the environmental impact of this process, obviating the necessity of disposing of the excess potassium carbonate, as well as other potassium salts.

The process of the invention may be described as follows. In the first step, while the phenyltriazolinone in a solvent such as 1-methyl-2-pyrrolidone, N,N-dimethylformamide, or N,N-dimethylacetamide is heated with potassium carbonate at a pot temperature in the range of about 120° to 140° C., water-containing distillate is removed from the reaction. This distillation may be carried out at atmospheric pressure, but preferably is done under a vacuum of 270-330 mm of mercury. While the presence of some water appears not to affect the ultimate yield, as shown below, the distillation serves to remove most of the water introduced with the potassium carbonate and the starting material, as well as that which is generated by the reaction of the potassium carbonate with the phenyltriazolinone. During the reaction, the potassium carbonate disproportionates, releasing both carbon dioxide and water and regenerating potassium carbonate. This is summarized in the following equations:

2 phenyltriazolinone + 2 $K_2CO_3 \rightarrow$ 2 $K$ + phenyltriazolinone + 2 $KHCO_3$ 2 $KHCO_3 \rightarrow K_2CO_3 + H_2O + CO_2$ The distillation temperature under the conditions set forth above is high enough to bring about this disproportionation.

In theory, one mole of potassium carbonate is required to react with two moles of triazolinone, but in practice some excess is required for the reaction to go to completion. Thus, only 0.5 mole of potassium carbonate is required to convert one mole of phenyltriazolinone to its potassium salt. However, the presence of some potassium carbonate is required in the second step for good yields of the difluoromethylated product.

After the potassium salt of the triazolinone has been formed and water distilled off, the salt and solvent are heated to 110° to 180° C., preferably 120° to 160° C., in a closed system and a 10 to 15 percent molar excess of chlorodifluoromethane is added. The reaction mixture is then heated at 140° to 210° C., preferably 160° to 200° C., for 5 to 60 minutes, after which the reactor is cooled and the difluoromethylated triazolinine is recovered. These and other aspects of the invention are demonstrated in the examples that follow.

Example 1

Effect of Molar Equivalents of Potassium Carbonate

A solution of 41.1 grams (0.232 mole) of 4,5-dihydro-3-methyl-1-phenyl-1H-1,2,4-triazol-5-one (99% purity) in 470 grams of N,N-dimethylformamide was placed in a flask fitted with a fractionating column. To this vigorously stirred solution was added 43.6 grams (0.185 mole) of a 48% aqueous solution of potassium carbonate, causing a 3° C. rise in the temperature of the reaction mixture. An additional 4.9 grams of water was added as a rinse to the flask from which the potassium carbonate solution had been added. The reaction mixture was then heated for distillation. The first distillate from the reaction mixture was water (cut 1, weighing 36.6 grams) and was followed by a mixture of water and N,N-dimethylformamide (cut 2, weighing 30.1 grams). The third cut (27.1 grams) was identified as N,N-dimethylformamide. This atmospheric distillation required 2.5 hours. The contents of the reaction flask were transferred to a 1 liter autoclave, which was heated to 120° C. The addition of 24.1 grams (0.279 mole) of chlorodifluoromethane to the autoclave required less than 4 minutes and caused the temperature to rise 8° C. Once the addition was complete, the reaction mixture was heated at 150° C. for one hour to complete the reaction and decompose any unreacted chlorodifluoromethane. After cooling and removal from the autoclave, the reaction mixture was filtered to remove solid salts, and the filter cake was washed with 300 mL of N,N-dimethylformamide. Gas chromatographic analysis of the filtrate showed that it was composed of 1.7% 5-fluoro-3-methyl-1-phenyl-1H-1,2,4-triazole, 2.4% 5-difluoromethoxy-3-methyl-1-phenyl-1H-1,2,4-triazole, and 94.8% 4-difluoromethyl-4,5-dihydro-3-methyl-1-phenyl-1H-1,2,4-triazol-5-one (calculated as area percent, excluding the solvent). A 1.6264 gram sample of the filtrate was placed in 10 mL of tetrahydrofuran, and 0.1004 gram of heptadecane was added as an internal standard to determine the yield by gas chromatography. The yield calculated in this manner for this reaction was 91.5%. This reaction is included in Table 1 as run 1B. The same general reaction procedure was followed in all examples tabulated in Table 1, except 1E and 1F, in which cases the salt of the triazolinone was prepared by reaction with KOH and then was oven dried prior to being introduced into the N,N-dimethylformamide for the second step.

In run 1E no additional potassium carbonate was added to the reaction mixture before reaction with chlorodifluoromethane, whereas in run 1F 1.268 moles of potassium carbonate per mole of phenyltriazolinone was added. In run 1E a large amount of starting material remained unreacted, a fact reflected by a yield that is 15% lower than was realized in run 1F. This clearly demonstrates the need for potassium carbonate to be present during the reaction with chlorodifluoromethane. Runs 1A, 1B, 1C, and 1D demonstrate that a wide range of molar ratios of potassium carbonate to phenyltriazolinone give satisfactory yields, going down to at least as low as about 0.60, but with some apparent advantage for about 0.8. However, for environmental reasons the ratio should be as low as practicable without significant loss of yield.

There does not appear to be any difference in yield between the use of solid potassium carbonate and a 47% aqueous solution of potassium carbonate. The primary consideration is the ease with which one or the other is handled in the equipment in which the reaction is carried out. Otherwise, it simply requires longer to remove the excess water added when the 47% aqueous solution is used.

Example 2

Effect of Step 2 Conditions

A 17.33 weight percent solution of 4,5-dihydro-3-methyl-1-phenyl-1H-1,2,4-triazol-5-one in N,N-dimethylformamide weighing 500 grams (0.495 mole) was placed in a flask fitted with a fractionating column. To this vigorously stirred solution was added dropwise 116.3 grams (0.396 mole) of a 47% aqueous solution of potassium carbonate. This addition required 10 minutes, during which the pot temperature rose from 25° C. to 31° C. The reaction mixture was then heated under a moderate vacuum, between 330 and 350 mm of mercury. Water distilled from the reaction mixture first and was followed by a mixture of water and N,N-dimethylformamide. The vacuum was controlled so that the pot temperature did not exceed 135° C. This distillation required 5 hours and was considered complete when the head temperature had reached about 125° C. and essentially no further distillate was observed during a period of 30 minutes. The distillate was weighed, and from this weight was subtracted the amount of water produced in the reaction plus the water introduced with the potassium carbonate initially. In this way the amount of N,N-dimethylformamide removed by the distillation was calculated. An equivalent amount of dry N,N-dimethylformamide was then used to rinse the reaction flask in which the potassium salt had been prepared, and the rinse was added to the reaction mixture, which had been placed in a 1 liter autoclave. The autoclave was sealed, and heating was initiated. After the contents of the autoclave were heated to 160° C., 48.15 grams (0.557 mole) of chlorodifluoromethane was added during a 3 minute period, causing the temperature to rise to 172° C. Upon completion of the addition, the reaction mixture was heated at 175° C. for one hour to complete the reaction and decompose any unreacted chlorodifluoromethane. After being cooled and removed from the autoclave, the reaction mixture was filtered to remove solid salts. The filter cake was washed with N,N-dimethylformamide until the filtrate was colorless, and all filtrates were combined. A 0.757 gram sample of the filtrate was placed in 10 mL of tetrahydrofuran, and 0.1 gram of heptadecane was added as an internal standard to determine the weight/weight yield by gas chromatography. The yield calculated in this manner for this reaction was 96.81%. This reaction is included in Table 2 as run 2C. This typical reaction procedure was followed in all runs tabulated in Table 2.

Runs 2A through 2H, reported in Table 2, show the effects on yield of varying molar excess of chlorodifluoromethane, feed rate of chlorodifluoromethane, feed temperature, and hold temperature. Run 2A utilized only a 5% excess of chlorodifluoromethane and produced the lowest yield, 83.73%, but this may be partially attributable to the low hold temperature of 120° C. Comparison of 2A with 2D suggests the lower yield in 2A may well be caused by insufficient chlorodifluoromethane. Going beyond the 20% excess used in runs 2D through 2H appears to be wasteful and environmentally unsound. Good yields have been achieved with an excess of about 12.5% chlorodifluoromethane, as shown by run 2C and confirmed in runs carried out on a larger scale. Although yield does not significantly depend on the time required to feed the chlorodifluoromethane into the reaction mixture, feeding it as rapidly as possible does appear to be desirable. In this way productivity is increased, and yield may actually be increased slightly. The apparent lack of dependence on feed rate seems to indicate that the reaction is very fast. The feed temperature may have some effect, particularly increasing yield at or above a temperature of 160° C. Runs on a larger scale confirm that this temperature, or one close to it, is the preferred temperature. A factor which does appear to be involved in maximizing yield is the hold temperature, with 160° to 200° C. being preferred. The reaction of the chlorodifluoromethane appears to be very rapid. (One run at 2000° C. with a hold time of only two minutes gave a yield of 95.62%.) In these runs the length of the hold time has been arbitrarily selected as one hour. This hold time may be longer than necessary and serves only to assure the destruction of the unreacted excess chlorodifluoromethane, clearly an environmental benefit, since chlorodifluoromethane is a chlorofluorohydrocarbon implicated in the destruction of the ozone layer.

Example 3

Effect of Distillation Pot Temperature

In a flask fitted with a fractionating column was placed 224.1 grams (0.257 mole) of a 20.1 weight percent solution of 4,5-dihydro-3-methyl-1-phenyl-1H-1,2,4-triazol-5-one in N,N-dimethylformamide. An additional 282.9 g of N,N-dimethylformamide was added to the flask, reducing the concentration to 8.55 weight percent. To this vigorously stirred solution was added 60.5 grams (0.206 mole) of a 47% aqueous solution of potassium carbonate. The reaction mixture was then heated under a vacuum of 270 mm of mercury, causing the water from the potassium carbonate solution and that generated by the reaction of the potassium carbonate with the 4,5-dihydro-3-methyl-1-phenyl-1H-1,2,4-triazol-5-one to distill from the reaction mixture, along with some N,N-dimethylformamide. The distillation required 7.2 hours, during which time 81.2 grams of distillate was collected, and the maximum pot temperature was 125° C. The amount of water in the distillate was calculated to be 34.4 grams. From this calculation, it was determined that 46.8 grams of N,N-dimethylformamide had distilled with the water. The entire reaction mixture was then placed in a 1 liter autoclave. An additional 46.8 grams of fresh, dry N,N-dimethylformamide was used to rinse the flask in which the first step had been run, and this rinse was added to the mixture in the autoclave before the autoclave was sealed and the second step was initiated. The mixture was heated to 119° C., at which temperature the addition of 23.3 grams (0.270 mole) of chlorodifluoromethane began. This addition required 2 minutes, during which time the temperature rose to 127° C. The reaction mixture was then heated to 150° C. and held at this temperature for one hour to complete the reaction and to decompose any unreacted chlorodifluoromethane. At the conclusion of this period the reaction mixture was cooled and filtered. The filter cake was washed with approximately 400 mL of N,N-dimethylformamide, and these washings were combined with the filtrate. Gas chromatographic analysis of the filtrate provided the following composition: 0.1% 5-fluoro-3-methyl-1-phenyl-1H-1,2,4-triazole, 1.45% 5-difluoromethoxy-3-methyl-1-phenyl-1H-1,2,4-triazole, 0.14% 4,5-dihydro-3-methyl-1-phenyl-1H-1,2,4-triazol-5-one, and 94.5% 4-difluoromethyl-4,5-dihydro-3-methyl-1-phenyl-1H-1,2,4-triazol-5-one (calculated as area percent, excluding the solvent). By the procedure described in Example 1, the yield of 4-difluoromethyl-4,5-dihydro-3-methyl-1-phenyl-1H-1,2,4-triazol-5-one was determined by gas chromatography to be 92.5%. This reaction is included in Table 3 as run 3B. All runs tabulated in Table 3 were run according to the same general procedure, but differed in the way in which water was removed.

Runs 3A through 3D in Table 3 were carried out under moderate vacuum (270 to 400 mm of mercury). Run 3E was distilled at atmospheric pressure. There may be some adverse effect of a maximum temperature of 141° C. on yield as seen in run 3D, but it is small and may well be within experimental error. However, the atmospheric pressure distillation at 160° C. in run 3E caused nearly a 20% reduction in yield.

Another factor affecting the yield may be the concentration of the phenyltriazolinine in N,N-dimethylformamide (DMF). All the runs reported in Table 1, where good yields were obtained, were distilled at atmospheric pressure, and the concentration of phenyltriazolinone in DMF was about 9 weight percent. In the runs reported in Table 3, good yields were obtained in runs 3A, 3C, and 3D, distilled under reduced pressure, with a phenyltriazolinone concentration of about 20 weight percent, whereas run 3E, at 20 weight percent concentration, distilled at atmospheric pressure, gave a poor yield. It appears that for atmospheric distillation a phenyltriazolinone concentration of under about ten weight percent is best, while when distillation is under reduced pressure, good yields are obtained at significantly higher concentrations. As a practical matter, in commercial production the temperature must be high enough not only to remove the water within a reasonable period of time, consistent with satisfactory yields, but also high enough to complete the disproportionation of $KHCO_3$, since the presence of bicarbonate in the second step has an adverse effect on yields.

Example 4

Effect of the Presence of Water

In a flask was placed 500 grams (0.495 mole) of a 17.33 weight percent solution of 4,5-dihydro-3-methyl-1-phenyl-1H-1,2,4-triazol-5-one in N,N-dimethylformamide. The flask was fitted with a fractionating column and was vigorously stirred. To this flask was added portionwise 54.7 grams (0.396 mole) of solid potassium carbonate at a rate to avoid agglomeration of the solid material. Upon completion of addition, the reaction mixture was heated under a vacuum of 330 to 350 mm of mercury, causing the water generated by the reaction of the potassium carbonate with the 4,5-dihydro-3-methyl-1-phenyl-1H-1,2,4-triazol-5-one to distill at a head temperature of 85° C. The distillation required 4.67 hours concluding at a head temperature of 124° C. During the distillation 72 grams of distillate was collected, and the maximum pot temperature was maintained below 135° C. by adjusting the vacuum. The calculated amount of water generated by this reaction was 4.5 grams. From this calculation, it was determined that 67.5 grams of N,N-dimethylformamide had distilled with the water. Immediately, 20.1 grams of fresh, dry N,N-dimethylformamide was restored to the reaction mixture. The entire reaction mixture was then placed in a 1 liter autoclave.

Before sealing the autoclave an additional 47.4 grams of fresh, dry N,N-dimethylformamide was used to rinse the flask in which Step 1 had been run, and this rinse was added to the mixture in the autoclave before proceeding with Step 2. Also, just prior to running Step B, a sample of the reaction mixture was analyzed by gas chromatography for its water content. This analysis indicated the water content to be 700 ppm. The mixture was heated to 160° C. in the sealed autoclave at which temperature the addition of 48.8 grams (0.564 mole) of chlorodifluoromethane commenced. This addition required 6 minutes, during which the temperature rose to 172° C. The reaction mixture was then heated to 175° C. and held at this temperature for one hour to complete the reaction and to decompose any unreacted chlorodifluoromethane. Upon removal from the autoclave, the reaction mixture was filtered, and the filter cake was washed with N,N-dimethylformamide. Gas chromatographic analysis of the combined filtrate and wash showed that it was composed of 1.27% 5-fluoro-3-methyl-1-phenyl- 1H-1,2,4-triazole, 0.55% 5-difluoromethoxy-3-methyl-1-phenyl-1H-1,2,4-triazole, 1.44% molecular weight 332 (dimer), 95.90% 4-difluoromethyl-4,5-dihydro-3-methyl-1-phenyl-1H-1,2,4-triazol-5-one, and 0.84% unidentified material (calculated as area percent, excluding the solvent). Using the procedure described in Example 1, the yield of 4-difluoromethyl-4,5-dihydro-3-methyl-1-phenyl-1H-1,2,4-triazol-5-one was determined by gas chromatography to be 92.23%. This reaction is included in Table 4 as Experiment Number 4E. This procedure is typical of all experiments tabulated in Table 4 with the exception that in some reactions a 47% by weight solution of potassium carbonate in water was substituted for the solid potassium carbonate.

Table 4 addresses the amount of water that can remain in the reaction system at the conclusion of the distillation without significantly affecting yield. Excluding Example 4C, the results of all of these experiments indicate that an amount of water between <200 ppm and 1600 ppm does not have a significant effect on the ultimate yield of product. However, run 4J, with 2400 ppm of water, shows a substantial reduction in yield.

Example 4C in Table 4 shows that impurities in the 4,5-dihydro-3-methyl-1-phenyl-1H-1,2,4-triazol-5-one can have a significant effect on the ultimate yield. In this example the starting material was incompletely washed with water, leaving 10% residual salts from the triazolinone synthesis present during Step 2. A significant amount of starting material remained unreacted, depressing the Step 2 yield to 64.53%.

Example 5

Use of other Starting Materials

In a flask were placed 50.0 grams (0.220 mole) of 4,5-dihydro-1-(4-chloro-2-fluorophenyl)-3-methyl-1H-1,2,4-triazol-5-one (96.5% purity) and 450 grams of N,N-dimethylformamide. To this flask, which was fitted with a distillation column and was vigorously stirred, was added dropwise 51.7 grams (0.176 mole) of a 47% aqueous solution of potassium carbonate. The reaction mixture was heated under a vacuum of 100 mm of mercury to distill off the water. A total of 72.4 grams of distillate was collected during the distillation which required 4.5 hours. The maximum pot temperature during the distillation was 96° C. The reaction mixture was then transferred to a 1 liter autoclave, and a total of 38 grams of N,N-dimethylformamide was used to rinse the reaction flask. These rinses were added to the autoclave before it was sealed. The reaction mixture was heated to 120° C., at which temperature 22.8 grams (0.26 mole) of chlorodifluoromethane was added over a two minute period, during which the temperature rose to 128° C. Upon completion of the addition, the reaction mixture was heated to 150° C. and held at this temperature for one hour to assure completion of reaction and destruction of excess chlorodifluoromethane. After being cooled to room temperature, the reaction mixture was filtered, and the filter cake was washed with approximately 300 mL of N,N-dimethylformamide. The combined filtrate and wash were analyzed by gas chromatography, yielding the following composition: 5.0% 5-difluoromethoxy-1-(4-chloro-2-fluorophenyl)3-methyl-1H-1,2,4-triazole, 89.4% 4-difluoromethyl-1-(4-chloro-2-fluorophenyl)-4,5-dihydro-3-methyl-1H-1,2,4-triazol-5-one, and 1.8% 4,5-dihydro-1-(4-chloro-2-fluorophenyl)-3-methyl-1H-1,2,4-triazol-5-one. By the method described in Example 1, a yield of 69.2% was calculated by gas chromatography using an internal standard. A portion of the filtrate (approximately 150 mL) was poured into 1 liter of water, forming a precipitate weighing 5 grams. This was recovered by filtration. The filtrate was then concentrated to a volume of about 200 mL, which was then added to 1.3 liters of water, this time forming a precipitate weighing 36 grams. This precipitate was recovered by filtration, and the two combined precipitates were dissolved in 1250 mL of ethanol at 80° C., which was then allowed to cool. The precipitate that formed was removed by filtration, and the solid washed with ethanol. After being air-dried, the brown crystals of 4,5-dihydro-1-(4-chloro-2-fluorophenyl)-3-methyl-1H-1,2,4-triazol-5-one weighed 24 grams. These were recrystallized a second time in ethanol. After being recovered by filtration, the solid was dried under vacuum, yielding 17.3 grams of 4,5-dihydro-1-(4-chloro-2-fluorophenyl)-3-methyl-1H-1,2,4-triazol-5-one as tan crystals, m.p. 115° C. and 99.9% purity. This is Example Number 5C in Table 5. The remaining examples were run according to the procedure described, utilizing the indicated starting material. Also, in Example Numbers 5F and 5G the N,N-dimethylformamide was replaced by 1-methyl-2-pyrrolidone and N,N-dimethylacetamide, respectively.

Table 5 provides examples of the use of the process starting with 4-chloro-2-fluorophenyltriazolinone and 2-fluorophenyltriazolinone. In all of these cases the yields are not as good as those when the starting material is 4,5-dihydro-3-methyl-1-phenyl-1H-1,2,4-triazol-5-one, probably because the halogens on the phenyl ring affect the reactivity and, therefore, the ultimate yield of the difluoromethylated triazolinone. As seen from the examples in Table 5, the yield is still high enough to be commercially useful. Nearly all of these examples were carried out in N,N-dimethylformamide. Two, Examples 5F and 5G, utilized 1-methyl-2-pyrrolidone and N,N-dimethylacetamide, respectively, as possible alternative solvents.

Example 6

Scaleup of the Process

In an 1892.5 liter, glass-lined reactor was placed 763.4 kilograms of a 17.3% by weight (as determined by gas chromatographic analysis using an internal standard) solution of 4,5-dihydro-3-methyl-1-phenyl-1H-1,2,4-triazol-5-one (132.1 kilograms, 0.754 kilogram-mole)in N,N-dimethylformamide. To the reactor was then added an additional 560 kilograms of N,N-dimethylformamide. During a 25 minute period 179.2 kilograms of a 47% aqueous solution of potassium carbonate (84.2 kilograms, 0.609 kilogram-mole) was added while the reactor contents were being agitated at 100 RPM at 25° C. The reactor was then heated under a vacuum of 270–284 mm of mercury to distill the water from the reaction mixture. Initially, the head temperature was 73° C., and this rose to 94°–95° C. after 13 hours. A cut, which weighed 113.4 kilograms and consisted primarily of water, was taken at this point. Distillation was resumed, and the head temperature gradually rose to 113.7°–113.9° C. When head temperature remained steady without further distillate being observed, the distillation was terminated. This portion of the distillation lasted for 3.5 hours and yielded distillate which weighed 59.4 kilograms and was a combination of water and N,N-dimethylformamide. Analysis of the contents of the reactor showed that the water content was below 200 ppm. Access to the distillation column was then closed off, the reaction mixture was heated to 157° C., and 88.2 kilograms (1.02 kilogram-moles) of chlorodifluoromethane was added during a 17 minute period. The temperature rose to 178.8° C. during this addition. For a period of one hour the temperature was maintained at 174°–180° C to complete the reaction and destroy any unreacted chlorodifluoromethane, after which the reaction mixture was cooled to 40° C. At this temperature the mixture was sparged with nitrogen for a period of 80 minutes, after which it was centrifuged to remove potassium salts. The filter cake was washed with 91.9 kilograms of N,N-dimethylformamide. This wash was combined with the filtrate, providing a solution of 4-difluoromethyl-4,5-dihydro-3-methyl-1-phenyl-1H-1,2,4-triazol-5-one weighing 1278.2 kilograms. Gas chromatographic analysis of this solution, by use of an internal standard, indicated that it contained 157.8 kilograms of 4-difluoromethyl-4,5-dihydro-3-methyl-1-phenyl-1H-1,2,4-triazol-5-one, a yield of 93.1% based on the weight of 4,5-dihydro-3-methyl-1-phenyl-1H-1,2,4-triazol-5-one charged to the reactor.

It is apparent that various modifications may be made in the process of this invention without departing from the inventive concepts of the process as defined in the claims.

TABLE 1

Effect of Molar Equivalents of Potassium Carbonate on Yield of Product

| Ex. No. | Molar Excess of $K_2CO_3$[a] | GC Analysis (Area Percent) | | | | | Yield[f] (%) | Comments |
|---|---|---|---|---|---|---|---|---|
| | | MW177[b] | O-isomer[c] | S.M. | MW332[d] | Product[e] | | |
| 1A | 0.108 | ND[g] | 3.6 | 2.0 | 0.47 | 91.3 | 87.8 | Solid, undried $K_2CO_3$ |
| 1B | 0.298 | 1.7 | 2.4 | ND | ND | 94.8 | 91.5 | 47% Aqueous $K_2CO_3$ |
| 1C | 0.500 | 0.4 | 1.6 | ND | 1.0 | 95.5 | 91.3 | Solid, undried $K_2CO_3$ |
| 1D | 3.146[h] | ND | 3.7 | ND | 0.8 | 94.2 | 89.8 | Solid, undried $K_2CO_3$ |
| 1E | 0 | ND | 6.3 | 11.9 | ND | 81.0 | 77.3 | Dried salt from KOH |
| 1F | 1.268 | ND | 2.1 | 0.5 | 2.1 | 93.2 | 92.4 | Dried salt from KOH |

[a]Molar excess of $K_2CO_3$ over that theoretically required to convert the starting material (S.M.), 4,5-dihydro-3-methyl-1-phenyl-1H-1,2,4-triazol-5-one, to its potassium salt.
[b]5-fluoro-3-methyl-1-phenyl-1H-1,2,4-triazole
[c]5-difluoromethoxy-3-methyl-1-phenyl-1H-1,2,4-triazole
[d]believed to be a dimer of 4,5-dihydro-3-methyl-1-phenyl-1H-1,2,4-triazol-5-one
[e]4-difluoromethyl-4,5-dihydro-3-methyl-1-phenyl-1H-1,2,4-triazol-5-one
[f]Yield calculated on a weight/weight basis by gas chromatography using an internal standard
[g]ND = not detected.
[h]One step - S.M. solution + base in autoclave. $H_2O$ not removed.

TABLE 2

Effect of Step 2 Conditions on Yield

| Exp. No. | Molar Excess[a] (%) | Freon Addition Conditions | | | | Yield[b] (%) |
|---|---|---|---|---|---|---|
| | | Feed Time (minutes) | Feed Temp. (°C.) | Hold Time (hours) | Hold Temp. (°C.) | |
| 2A | 5 | 61 | 100 | 1 | 120 | 83.73 |
| 2B | 12.5 | 32 | 118 | 1 | 135 | 91.34 |
| 2C | 12.5 | 5 | 160 | 1 | 175 | 96.81 |
| 2D | 20 | 3 | 100 | 1 | 120 | 89.09 |
| 2E | 20 | 2 | 80 | 1 | 150 | 89.15 |
| 2F | 20 | 3 | 139 | 1 | 150 | 92.22 |
| 2G | 20 | 3 | 160 | 1 | 175 | 96.57 |
| 2H | 20 | 57 | 180 | 1 | 200 | 93.91 |

[a]Based on moles of 4,5-dihydro-3-methyl-1-phenyl-1H-1,2,4-triazol-5-one initially charged to Step 1 for salt formation.
[b]Yield calculated on a weight/weight basis by gas chromatography utilizing an internal standard.

TABLE 3

Effect of Distillation Pot Temperature on Yield

| Ex. No. | Distillation[a] °C. | Hrs. | GC Analysis (Area Percent) | | | | | Yield[f] (%) | % S.M. in DMF |
|---|---|---|---|---|---|---|---|---|---|
| | | | MW177[b] | O-isomer[c] | S.M.[d] | MW332 | Product[e] | | |
| 3A | 125 | 6.3 | 0.8 | 4.4 | 0.3 | 0.4 | 91.4 | 91.2 | 20 wt. % |
| 3B | 125 | 7.2 | 0.1 | 1.5 | 0.1 | 1.0 | 94.5 | 92.5 | 8.55 wt. % |
| 3C | 125 | 13 | 0.8 | 3.5 | 0.2 | 0.3 | 93.2 | 92.0 | 20 wt. % |
| 3D | 141 | 5.2 | 0.3 | 4.1 | 0.5 | 1.4 | 91.5 | 89.6 | 20 wt. % |

TABLE 3-continued

Effect of Distillation Pot Temperature on Yield

| Ex. No. | Distillation[a] °C. | Hrs. | GC Analysis (Area Percent) | | | | | Yield[f] (%) | % S.M. in DMF |
|---|---|---|---|---|---|---|---|---|---|
| | | | MW177[b] | O-isomer[c] | S.M.[d] | MW332 | Product[e] | | |
| 3E | 160 | 8.5 | 0.1 | 5.6 | 14.4 | 1.9 | 77.0 | 70.3 | 20 wt. % |

[a] A 47% aqueous solution of K₂CO₃ was used in these experiments
[b] 5-fluoro-3-methyl-1 phenyl-1H-1,2,4-triazole
[c] 5-difluoromethoxy-3-methyl-1-phenyl-1H-1,2,4-triazole
[d] 4,5-dihydro-3-methyl-1-phenyl-1H-1,2,4-triazol-5-one
[e] 4-difluoromethyl-4,5-dihydro-3-methyl-1-phenyl-1H-1,2,4-triazol-5-one
[f] Yield calculated on a weight/weight basis by gas chromatography using an internal standard

TABLE 4

Effect of Residual Water on Step B

| Ex. No. | Base[a] | Water (ppm) | GC Analysis (Area Percent) | | | | | | Yield[f] (%) | Comments |
|---|---|---|---|---|---|---|---|---|---|---|
| | | | MW177[b] | O-isomer[c] | S.M.[d] | MW332 | Product[e] | Other | | |
| 4A | solid | <200 | 1.04 | 0.97 | 0.00 | 1.91 | 95.43 | 0.64 | 91.02 | 20% S.M. in DMF |
| 4B | solid | 200 | 0.75 | 0.37 | 0.00 | 1.49 | 97.16 | 0.24 | 93.06 | Step 2, 200°/10 min. |
| 4C | liquid | 400 | 0.00 | 0.67 | 21.67 | 4.41 | 71.41 | 1.84 | 64.53 | 10% salts in S.M. |
| 4D | liquid | 400 | 0.26 | 1.66 | 0.00 | 0.96 | 97.12 | 0.00 | 95.62 | Step 2, 200°/2 min |
| 4E | solid | 700 | 1.27 | 0.55 | 0.00 | 1.44 | 95.90 | 0.84 | 92.23 | Step 2, 175°/1 hr. |
| 4F | liquid | 1000 | 0.00 | 0.82 | 0.18 | 4.24 | 93.81 | 0.95 | 92.10 | Step 2, 175°/1 hr. |
| 4G | liquid | 1200 | 0.00 | 0.63 | 0.00 | 6.11 | 92.66 | 0.59 | 90.98 | Step 2, 175°/1 hr. |
| 4H | solid | 1300 | 1.65 | 0.46 | 0.00 | 1.20 | 95.63 | 1.05 | 90.60 | Step 2, 175°/1 hr. |
| 4I | liquid | 1600 | 0.00 | 0.33 | 0.00 | 2.80 | 96.86 | 0.00 | 91.84 | Step 2, 175°/1 hr. |
| 4J | liquid | 2400 | 0.43 | 1.87 | 1.37 | 9.57 | 85.89 | 0.88 | 81.67 | Step 2, 175°/1 hr. |

[a] potassium carbonate utilized either as the solid material or a 47% by weight solution in water
[b] 5-fluoro-3-methyl-1-phenyl-1H-1,2,4-triazole
[c] 5-difluoromethoxy-3-methyl-1-phenyl-1H-1,2,4-triazole
[d] 4,5-dihydro-3-methyl-1-phenyl-1H-1,2,4-triazol-5-one
[e] 4-difluoromethyl-4,5-dihydro-3-methyl-1-phenyl-1H-1,2,4-triazol-5-one
[f] yield calculated on a weight/weight basis by gas chromatography using an internal standard

TABLE 5

Use of Other Starting Materials and Solvents in this Process

| Ex. No. | Starting Materials (S.M.) | Temperatures | | GC Analysis (Area Percent) | | | Yield[f] (%) |
|---|---|---|---|---|---|---|---|
| | | Distillation °C. | Reaction °C.[b] | O-isomer[c] | S.M.[d] | Product[e] | |
| 5A | 4Cl,2F-phenyltriazolinone[g] | 122 | 180 | 0.3 | 0.5 | 93 | 81.1 |
| 5B | 4Cl,2F-phenyltriazolinone | 122 | 150 | 3.7 | 0.1 | NA | 75.6 |
| 5C | 4Cl,2F-phenyltriazolinone | 96[h] | 120 | 5.0 | 1.8 | 89.4 | 69.2 |
| 5D | 4Cl,2F-phenyltriazolinone | 122 | 110 | 8.6 | 3.5 | 81 | 62.5 |
| 5E | 2F-phenyltriazolinone[i] | 121 | 170 | 7.8 | 0.7 | 85 | 54 |
| 5F | 2F-phenyltriazolinone[j] | 140 | 175 | NA | NA | NA | 61 |
| 5G | 2F-phenyltriazolinone[k] | 109 | 170 | NA | NA | NA | 74 |

[a] Maximum pot temperature
[b] Temperature at which chlorodifluoromethane is injected into autoclave
[c] 5-difluoromethoxy-1-(4-chloro-2-fluorophenyl)-3-methyl-1H-1,2,4-triazole or 5-difluoromethoxy-(2-fluorophenyl)-3-methyl-1-1H-1,2,4-triazole
[d] 4,5-dihydro-1-(4-chloro-2-fluorophenyl)-3-methyl-1H-1,2,4-triazol-5-one or 4,5-dihydro-(2-fluorophenyl)-3-methyl-1-1H-1,2,4-triazol-5-one (see comments for identification)
[e] 4-difluoromethyl-1-(4-chloro-2-fluorophenyl)-4,5-dihydro-3-methyl-1H-1,2,4-triazol-5-one or 4-difluoromethyl-4,5-dihydro-1-(2-fluorophenyl)-3-methyl-1H-1,2,4-triazol-5-one
[f] Yield calculated on a weight/weight basis by gas chromatography using an internal standard
[g] 4,5-dihydro-1-(4-chloro-2-fluorophenyl)-3-methyl-1H-1,2,4-triazol-5-one
[h] Distillation lasted for 4 hours
[i] 4,5-dihydro-1-(2-fluorophenyl)-3-methyl-1H-1,2,4-triazol-5-one
[j] Solvent used was 1-methyl-2-pyrrolidone
[k] Solvent used was N,N-dimethylacetamide

We claim:

1. In a process for the difluoromethylation of a 1-phenyl-1H-1,2,4-triazol-5-one (the triazolinone) at the 4-position of the triazole ring with chlorodifluoromethane, the improvement that comprises
   (a) reacting the triazolinone with potassium carbonate in a solvent selected from dimethylformamide, 1-methyl-2-pyrrolidone, and N,N-dimethylacetamide at a carbonate to triazolinone ratio in the range of about 0.55 to 1.0;
   (b) reducing the water content of the reaction mixture to below about 2400 ppm by distillation;
   (c) in a sealed autoclave, heating the reaction mixture to 110° to 180° C., adding a 10 to 15 percent molar excess of chlorodifluoromethane, heating the reaction mixture at a temperature of 140° to 210° C. for 5 to 60 minutes, and recovering the difluoromethylated triazolinone.

2. A process of claim 1 in which the triazolinone is 4,5-dihydro-1-phenyl-3-methyl-1H-1,2,4-triazol-5-one, 4,5-dihydro-1-(4-chloro-2-fluorophenyl)-3-methyl-1H-1,2,4-triazol-5-one, or 4,5-dihydro-1-(2-fluorophenyl)-3-methyl-1H-1,2,4-triazol-5-one.

3. A process of claim 2 in which the triazolinone is 4,5-dihydro-1-phenyl-3-methyl-1H-1,2,4-triazol-5-one, and the solvent is dimethylformamide.

4. A process of claim 3 in which the distillation is carried out at a pot temperature in the range of 120° to 140° C., the reaction mixture is heated to 120° to 160° C. before addition of the chlorodifluoromethane and to 160° to 200° C. after the addition.

5. A process of claim 4 in which the ratio of carbonate to triazolinone is in the range of 0.65 to 0.85, and the distillation is carried out under reduced pressure.

* * * * *